US009282737B2

(12) United States Patent
Koshio et al.

(10) Patent No.: US 9,282,737 B2
(45) Date of Patent: Mar. 15, 2016

(54) AGENT FOR PREVENTING POLLEN DISPERSAL

(75) Inventors: Kaihei Koshio, Tokyo (JP); Hirokazu Ohike, Amagasaki (JP); Masahiko Shimada, Amagasaki (JP); Daijiro Shiino, Amagasaki (JP); Kuniaki Tsuruoka, Amagasaki (JP); Aiko Yamanaka, Amagasaki (JP)

(73) Assignee: NOF Corporation, Tokyo (JP)

( * ) Notice: Subject to any disclaimer, the term of this patent is extended or adjusted under 35 U.S.C. 154(b) by 840 days.

(21) Appl. No.: 12/866,446

(22) PCT Filed: Feb. 6, 2009

(86) PCT No.: PCT/JP2009/052101

§ 371 (c)(1), (2), (4) Date: Nov. 1, 2010

(87) PCT Pub. No.: WO2009/099212

PCT Pub. Date: Aug. 13, 2009

(65) Prior Publication Data

US 2011/0045981 A1 Feb. 24, 2011

(30) Foreign Application Priority Data

Feb. 8, 2008 (JP) ................................ 2008-028253
Feb. 8, 2008 (JP) ................................ 2008-028254
Feb. 18, 2008 (JP) ................................ 2008-036632
Feb. 18, 2008 (JP) ................................ 2008-036633

(51) Int. Cl.
*A01N 37/06* (2006.01)
*A01G 7/06* (2006.01)
*C07C 57/02* (2006.01)

(52) U.S. Cl.
CPC *A01N 37/06* (2013.01); *A01G 7/06* (2013.01); *C07C 57/02* (2013.01)

(58) Field of Classification Search
CPC ........... A01N 37/06; A01G 7/06; C07C 57/02
USPC ........................................................ 504/313
See application file for complete search history.

(56) References Cited

U.S. PATENT DOCUMENTS

| | | | |
|---|---|---|---|
| 2,322,820 | A | 6/1943 | Brown |
| 2011/0099664 | A1 | 4/2011 | Takagi et al. |

FOREIGN PATENT DOCUMENTS

| | | | |
|---|---|---|---|
| CN | 1878463 A | 12/2006 |
| JP | 04-099416 A | 3/1992 |
| JP | 05-238902 A | 9/1993 |
| JP | 07-053307 A | 2/1995 |
| JP | 10-098941 A | 4/1998 |
| JP | 2005-008576 A | 1/2005 |
| WO | WO 01/28961 A2 | 4/2001 |

OTHER PUBLICATIONS

Rheodol AO-10, Fatty Acid Esters with Polyhydric Alcohol and Their Derivatives. [online]. KAO, 2006 [retrieved on Dec. 12, 2012]. Retrieved from the Internet<http://web.archive.org/web/20060831150908/http://www.kao.com.sg/ester3a.htm>, 2 pages.*

Ota et al, Pollen Dispersion Inhibitor and Method for Preventing Dispersion of Pollen, JP-05-238902, Machine Translation, 10 pages.*

Test Plan for the Sorbitan Esters Category of the Aliphatic Esters Chemicals, Nov. 2003, American Chemistry Council's Aliphatic Esters Panel, pp. 1-28.*

Koshio et al., *Journal of Forest Research*, 5(2): 77-80 (May 16, 2000).

Gilchrist, Database CA Accession No. 17: 22976 (2001).

Hatanaka, Database CA Accession No. 109: 53149 (1988).

Chinese Patent Office, Search Report in Chinese Patent Application No. 200980112269.6 (Oct. 10, 2012).

Chinese Patent Office, First Office Action in Chinese Patent Application No. 200980112269.6 (Oct. 10, 2012).

European Patent Office, Extended European Search Report in European Patent Application No. 09708150.9, (Nov. 14, 2012).

International Bureau of WIPO, International Preliminary Report on Patentability in International Patent Application No. PCT/JP2009/052101 (Aug. 10, 2010).

Japanese Patent Office, International Search Report in International Patent Application No. PCT/JP2009/052101 (Mar. 3, 2009).

* cited by examiner

*Primary Examiner* — John Pak
*Assistant Examiner* — Andriae M Holt
(74) *Attorney, Agent, or Firm* — Leydig, Voit & Mayer, Ltd.

(57) ABSTRACT

An agent for suppressing pollen dispersal, containing an oleic acid derivative or a linoleic acid derivative as an active ingredient, which does not influence the trunk, branches and leaves of trees, shows a sharp efficacy on the male organ and is in the form of a solution or emulsion having solution stability by diluting with water.

7 Claims, No Drawings

AGENT FOR PREVENTING POLLEN DISPERSAL

TECHNICAL FIELD

The present invention relates to an agent for suppressing pollen dispersal, which suppresses dispersion of pollen from plants.

BACKGROUND ART

Of the pollens present in the male organ of plants, anemophilous pollen is dispersed in the air by being carried on the wind, and attaches to the ovule for pollination. When people inhale the pollen, a severe symptom called pollinosis is sometime developed. Particularly, in pollinosis due to pollen of *Cryptomeria, Chamaecyparis, Ambrosia* and the like, allergic conditions of the eye and nose are developed. The number of people suffering from the pollinosis tends to increase every year.

As a solution for such damages by pollen, administration of antihistamine agents, adrenal cortex hormone and the like, and use of eye drops, wearing masks and the like can be mentioned. The most effective solution is suppressing dispersal of pollen into the air.

As a measure for suppressing dispersal of pollen into the air, cutting down causative trees and plants and weeding can be mentioned. However, cutting down trees and the like are problematic in that they not only require enormous labor but also cause an adverse influence such as destruction of natural environment and the like.

As a means for suppressing dispersal of pollen other than cutting down trees, spraying or applying a certain kind of agent onto the male organ has been proposed. As examples of such agent, vegetable oils and fats containing oleic acid or linoleic acid as a main component (e.g., patent document 1) and those containing sodium oleate (e.g., patent document 2) as an active ingredient have been proposed.

However, since these agents show a comparatively slow efficacy on male flower buds, they are defective in that the timing of spraying of the agent is limited to August when male flower buds are in the initial period of bud differentiation process.

patent document 1: JP-B-8-762 patent document 2: JP-B-2890162

DISCLOSURE OF THE INVENTION

Problems to be Solved by the Invention

Therefore, the present invention aims to provide an agent for suppressing pollen dispersal, which has a sharp action on the male organ and does not influence the trunk, branches and leaves of trees.

Means of Solving the Problems

The present inventors have conducted intensive studies and found that the above-mentioned object can be achieved, which resulted in the completion of the present invention. Accordingly, the present invention is as follows.

The first invention is an agent for suppressing pollen dispersal, comprising, as an active ingredient, an oleic acid derivative or linoleic acid derivative represented by the following formula (I)

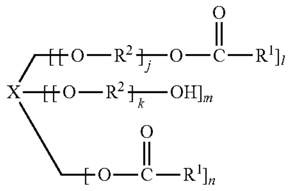

(I)

wherein $R^1$ are residues of an oleic acid ester or a linoleic acid ester, which may be of the same kind or different kinds, O—$R^2$ are oxyalkylene groups having a carbon number of 2 to 4, which may be of one kind of two or more kinds, and when they are of two or more kinds, they may be block adducts or random adducts;

when j+k is an integer of one or more and X is monovalent, then X is a hydrogen atom, a hydrocarbon group having a carbon number of 20 or below or an acyl group having a carbon number of 20 or below, j is an integer of 1-100, l=1 and m+n=0;

when j+k is an integer of one or more and X is a polyvalent organic group, then j and k are each an integer of 1-100, l+m+n is an integer of two or more and l+n is an integer of one or more;

when j and k are 0 and X is a polyvalent organic group having a carbon number of 3, then m+n is 3, l is 0 and n and m is 1 or 2; and when j and k are 0 and X is a polyvalent organic group having a carbon number of 4 or more, then l is 0, n is an integer of one or more, and m+n is an integer of two or more.

The second invention is the agent for suppressing pollen dispersal described in the first invention, wherein the oleic acid derivative or linoleic acid derivative is polyoxyethylene oleic acid ester or polyoxyethylene linoleic acid ester, or polyoxyethylene sorbitan oleic acid ester or polyoxyethylene sorbitan linoleic acid ester, or polyoxyethylene sorbitol oleic acid ester or polyoxyethylene sorbitol linoleic acid ester.

The third invention is an agent for suppressing pollen dispersal, which is an emulsion comprising the oleic acid derivative or linoleic acid derivative described in the second invention, which has an HLB of not more than 12, in a proportion of 0.5-30 wt %.

The fourth invention is an agent for suppressing pollen dispersal, which is an aqueous solution comprising the oleic acid derivative or linoleic acid derivative described in the second invention, which has an HLB of not less than 12, in a proportion of 0.5 wt% or above.

The fifth invention is the agent for suppressing pollen dispersal described in the first invention, wherein the oleic acid derivative or linoleic acid derivative is comprised of a partial ester of oleic acid or linoleic acid and glycerol.

The sixth invention is an agent for suppressing pollen dispersal, which is an emulsion comprising a partial ester of oleic acid or linoleic acid and glycerol in a proportion of 0.5-30 wt %.

The seventh invention is the agent for suppressing pollen dispersal described in the first invention, wherein the oleic acid derivative or linoleic acid derivative is comprised of an ester of oleic acid or linoleic acid and a polyvalent alcohol having a carbon number of not less than 4.

The eighth invention is an agent for suppressing pollen dispersal, which is an emulsion comprising an ester of oleic acid or linoleic acid and a polyvalent alcohol having a carbon number of not less than 4 in a proportion of 0.5-30 wt %.

The ninth invention is the agent for suppressing pollen dispersal described in the first invention, wherein the oleic acid derivative or linoleic acid derivative is comprised of an ester of oleic acid or linoleic acid and an alcohol having a sugar backbone.

The tenth invention is an agent for suppressing pollen dispersal, which is an emulsion comprising an ester of oleic acid or linoleic acid and an alcohol having a sugar backbone in a proportion of 0.5-30 wt %.

Effect of the Invention

The present invention can provide an agent for suppressing pollen dispersal, which has a sharp action on the male organ and does not influence the trunk, branches and leaves of trees. In addition, the form of an emulsion produced by diluting the agent for suppressing pollen dispersal of the present invention by adding water affords high solution stability.

BEST MODE FOR CARRYING OUT THE INVENTION

The agent for suppressing pollen dispersal of the present invention is explained in the following.

The present invention is an agent for suppressing pollen dispersal, comprising, as an active ingredient, an oleic acid derivative or linoleic acid derivative represented by the following formula (I)

(I)

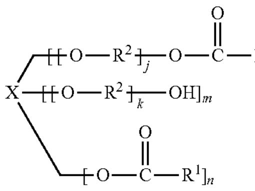

In the aforementioned formula (I), $R^1$ are residues of an oleic acid ester or linoleic acid ester, which may be of the same kind or different kinds. Fatty acid esters other than oleic acid and linoleic acid are not preferable, since some show an unsharp action on the male organ, and some influence the trunk, branches and leaves of trees, even though the action on the male organ is sharp.

In the aforementioned formula (I), O—$R^2$ are oxyalkylene groups having a carbon number of 2 to 4, which may be of one kind of two or more kinds, and when they are of two or more kinds, they may be block adducts or random adducts. O—$R^2$ are preferably oxyalkylene groups having a carbon number of 2 to 4. A compound having a carbon number of 1 is (poly) acetal having formaldehyde as a starting material, and is not preferable since the kind of the synthesis starting material is different, and develops formaldehyde as a decomposition product. In addition, alkylene oxide having a carbon number of not less than 5 is not preferable since the supplyability and reactivity of the starting material are low. Moreover, the oxyalkylene group represented by O—$R^2$ may be of one kind of two or more kinds, and when they are of two or more kinds, they may be block adducts or random adducts. When an ethylene oxide group having a carbon number of 2 is selected, HLB becomes higher, and then water-solubility can be imparted. On the other hand, as the carbon number increases, the oil-solubility becomes high and HLB becomes low, and therefore, the carbon number can be appropriately selected.

In the aforementioned formula (I), when j+k is an integer of one or more and X is monovalent, then X is a hydrogen atom, a hydrocarbon group having a carbon number of 20 or below, or an acyl group having a carbon number of 20 or below, j is an integer of 1-100, l=1 and m+n=0. When X is a monovalent organic group, X is a hydrocarbon group having a carbon number of 20 or below, or an acyl group having a carbon number of 20 or below. When the carbon number exceeds 20, supplyability becomes low even though the property does not change and unpreferably becomes expensive. j is an integer of 1-100. When it exceeds 100, the number of the oleic acid ester group or linoleic acid ester group becomes relatively small, and the action on the male organ is unpreferably lost. When X is monovalent, l=1 and m+n=0.

In the aforementioned formula (I), when j+k is an integer of one or more and X is a polyvalent organic group, then j and k are each an integer of 1-100, l+m+n is an integer of two or more, and l+n is an integer of one or more. When X is a polyvalent organic group, X is preferably a residue of an existing alcohol compound without a hydroxyl group, since it shows high supplyability. j and k are each an integer of 1-100. When they exceed 100, the number of oleic acid ester group or linoleic acid ester group becomes relatively small to lose action on the male organ, which is not preferable. When X is a polyvalent organic group, l+m+n is an integer of two or more, and l+n is an integer of one or more. When l+n=0, the oleic acid ester group and linoleic acid ester group are absent and the action on the male organ is unpreferably lost. While l+m+n may exceed 1000, it is not practical since the viscosity becomes high.

In the aforementioned formula (I), when j and k are 0 and X is a polyvalent organic group having a carbon number of 3, m+n is 3, l is 0 and n and m are each 1 or 2. When X is a polyvalent organic group having a carbon number of 3, the aforementioned formula (I) is preferably a partial ester of oleic acid or linoleic acid and glycerol. A partial ester of fatty acid other than oleic acid and linoleic acid and glycerol is not preferable, since it may show an unsharp action on the male organ, or may influence the trunk, branches and leaves of trees, even though the action on the male organ is sharp.

In the aforementioned formula (I), when j and k are each 0 and X is a polyvalent organic group having a carbon number of 4 or more, l is 0, n is an integer of one or more and m+n is an integer of two or more. When X is a polyvalent organic group having a carbon number of 4 or more, the aforementioned formula (I) is preferably an ester of oleic acid or linoleic acid and a polyvalent alcohol having a carbon number of 4 or more, more preferably, an ester of oleic acid or linoleic acid and an alcohol having a sugar backbone. An ester of fatty acid other than oleic acid and linoleic acid and a polyvalent alcohol having a carbon number of 4 or more is not preferable, since it may show an unsharp action on the male organ, or may influence the trunk, branches and leaves of trees, even though the action on the male organ is sharp.

For production of the aforementioned formula (I), when j+k is an integer of one or more and X is a hydrogen atom, a method including directly reacting oleic acid or linoleic acid with alkylene oxide is preferable, and when X is a hydrocarbon group having a carbon number of 20 or below, a method including reacting the corresponding alcohol with alkylene oxide, and adding oleic acid or linoleic acid to perform a general dehydrating reaction is preferable. On the other hand, when X is an acyl group having a carbon number of 20 or below, a method including reacting the corresponding carboxylic acid compound with alkylene oxide, and adding oleic acid or linoleic acid to perform a general dehydrating reaction, a method including directly reacting oleic acid or linoleic acid with alkylene oxide, and adding the corresponding carboxylic acid compound to perform a general dehydrating reaction, a method including adding polyalkylene glycol to the corresponding carboxylic acid compound and oleic acid or linoleic acid to perform a general dehydrating reaction and the like can be mentioned, and the method can be appropriately selected.

Specific examples of the obtained compound of the aforementioned formula (I) include polyoxyethylene oleic acid ester, polyoxyethylene linoleic acid ester, methoxypolyoxyethylene oleic acid ester, ethoxypolyoxyethylene linoleic acid ester, butyloxypolyoxyethylene oleic acid ester, hexyloxypolyoxyethylene linoleic acid ester, dodecyloxypolyoxyethylene oleic acid ester, lauryloxypolyoxyethylene linoleic acid ester, stearyloxypolyoxyethylene oleic acid ester, oleyloxypolyoxyethylene linoleic acid ester, polyoxyethylene oleic acid acetic acid ester, polyoxyethylene linoleic acid acetic acid ester, polyoxyethylene oleic acid butyric acid ester, polyoxyethylene linoleic acid caproic acid ester, polyoxyethylene oleic acid caprylic acid ester, polyoxyethylene lauric acid linoleic acid ester, polyoxyethylene oleic acid stearic acid ester, polyoxyethylene dilinoleic acid ester, polyoxyethylene-block-polyoxypropylene oleic acid ester, polyoxyethylene-ran-polyoxybutylene linoleic acid ester and the like.

On the other hand, for production of the aforementioned formula (I), when j+k is an integer of one or more and X is a polyvalent organic group, a method including reacting a polyvalent alcohol compound wherein the side chain of X is a hydroxyl group with alkylene oxide, and adding oleic acid or linoleic acid to perform a general dehydrating reaction, and a method including adding oleic acid or linoleic acid to a polyvalent alcohol compound to perform a general dehydrating reaction to give an ester, which is reacted with alkylene oxide can be mentioned, and the method can be appropriately selected.

Specific examples of the obtained compound of the aforementioned formula (I) include polyoxyethylene sorbitan oleic acid ester, polyoxyethylene sorbitan linoleic acid ester, polyoxyethylene sorbitol oleic acid ester, polyoxyethylene sorbitol linoleic acid ester, polyoxyethylene glycerol oleic acid ester, polyoxyethylene glycerol linoleic acid ester, polyoxyethylene diglycerol oleic acid ester, polyoxyethylene triglycerol linoleic acid ester, polyoxyethylene methylglucoside oleic acid ester, polyoxyethylene methylglucoside linoleic acid ester, polyoxyethylene-ran-polyoxypropylene sorbitan oleic acid ester, polyoxyethylene-block-polyoxybutylene sorbitan linoleic acid ester, polyvinyl alcohol-graft-(ω-oleinoyloxypolyoxyethylene) and the like.

For production of the aforementioned formula (I), when j and k are each 0 and X is a polyvalent organic group having a carbon number of 3, a trivalent alcohol compound wherein the side chain of X is a hydroxyl group and oleic acid or linoleic acid with an adjusted preparation molar ratio of 1-2 relative to 3 hydroxyl groups are subjected to a general dehydrating reaction, whereby it can be obtained.

Specific examples of the obtained compound of the aforementioned formula (I) include glycerol monooleate, glycerol dioletate, glycerol monolinolate and glycerol dilinolate. Here, when the aforementioned formula (I) is a partial ester of oleic acid or linoleic acid and glycerol, it can be obtained by adjusting the preparation molar ratio of fatty acid relative to glycerol. A triglyceride of fatty acid having a carbon number of not less than 8 wherein all three hydroxyl groups of glycerol are esterified is defective in that the timing of spraying of the agent is limited, since it shows a comparatively slow efficacy on male flower buds.

For production of the aforementioned formula (I), when j and k are each 0 and X is a polyvalent organic group having a carbon number of 4 or more, it can be obtained by appropriately adjusting the preparation molar ratios of oleic acid or linoleic acid and a polyvalent alcohol having a carbon number of 4 or more, and subjecting them to a general dehydrating reaction.

Specific examples of the obtained compound of the aforementioned formula (I) include 1,2-butanediol monooleate, 1,2-butanediol dioleate, 1,2-butanediol monolinolate, 1,2-butanediol dilinolate, 1,3-butanediol monooleate, 1,3-butanediol dioleate, 1,3-butanediol monolinolate, 1,3-butanediol dilinolate, 1,4-butanediol monooleate, 1,4-butanediol dioleate, 1,4-butanediol monolinolate, 1,4-butanediol dilinolate, pentaerythritol monooleate, pentaerythritol dioleate, pentaerythritol trioleate, pentaerythritol tetraoleate, pentaerythritol monolinolate, pentaerythritol dilinolate, pentaerythritol trilinolate, pentaerythritol tetralinolate, neopentylglycol, 1,5-pentanediol monooleate, 1,5-pentanediol dioleate, 1,5-pentanediol monolinolate, 1,5-pentanediol dilinolate, trimethylolethane monooleate, trimethylolethane dioleate, rtimethylolethane trioleate, trimethylolethane monolinolate, trimethylolethane dilinolate, trimethylolethane trilinolate, trimethylolpropane monooleate, trimethylolpropane dioleate, trimethylolpropane trioleate, trimethylolpropane monolinolate, trimethylolpropane dilinolate, trimethylolpropane trilinolate, 3-methyl-1,5-pentanediol monooleate, 3-methyl-1,5-pentanediol dioleate, 3-methyl-1,5-pentanediol monolinolate, 3-methyl-1,5-pentanediol dilinolate, 1,2-hexanediol monooleate, 1,2-hexanediol dioleate, 1,2-hexanediol monolinolate, 1,2-hexanediol dilinolate, 1,6-hexanediol monooleate, 1,6-hexanediol dioleate, 1,6-hexanediol monolinolate, 1,6-hexanediol dilinolate, 1,2,6-hexanetriol monooleate, 1,2,6-hexanetriol dioleate, 1,2,6-hexanetriol trioleate, 1,2,6-hexanetriol monolinolate, 1,2,6-hexanetriol dilinolate, 1,2,6-hexanetriol trilinolate, hexyleneglycol monooleate, hexyleneglycol dioleate, hexyleneglycol monolinolate, hexyleneglycol dilinolate, dipropyleneglycol monooleate, dipropyleneglycol dioleate, dipropyleneglycol monolinolate, dipropyleneglycol dilinolate, tripropyleneglycol monooleate, tripropyleneglycol dioleate, tripropyleneglycol monolinolate, tripropyleneglycol dilinolate, 2-butyl-2-ethyl-1,3-propanediol monooleate, 2-butyl-2-ethyl-1,3-propanediol dioleate, 2-butyl-2-ethyl-1,3-propanediol monolinolate, 2-butyl-2-ethyl-1,3-propanediol dilinolate, 2,2'-diethyl-2,2'-(oxydimethyl)bis(propane-1,3-diol) monooleate, 2,2'-diethyl-2,2'-(oxydimethyl)bis(propane-1,3-diol) dioleate, 2,2'-diethyl-2,2'-(oxydimethyl)bis(propane-1,3-diol)trioleate, 2,2'-diethyl-2,2'-(oxydimethyl)bis(propane-1,3-diol)tetraoleate, 2,2'-diethyl-2,2'-(oxydimethyl)bis(propane-1,3-diol) monolinolate, 2,2'-diethyl-2,2'-(oxydimethyl)bis(propane-1,3-diol) dilinolate, 2,2'-diethyl-2,2'-(oxydimethyl)bis(propane-1,3-diol) trilinolate, 2,2'-diethyl-2,2'-(oxydimethyl)bis(propane-1,3-diol) tetralinolate, diglycerol monooleate, diglycerol dioleate, diglycerol trioleate, diglycerol tetraoleate, diglycerol monolinolate, diglycerol dilinolate, diglycerol trilinolate, diglycerol tetralinolate, triglycerol monooleate, triglycerol dioleate, triglycerol trioleate, triglycerol tetraoleate, triglycerol pentaoleate, triglycerol monolinolate, triglycerol dilinolate, triglycerol trilinolate, triglycerol tetralinolate, triglycerol pentalinolate; oleic acid or linoleic acid esters of monosaccharides such as glucose, fructose and the like; oleic acid or linoleic acid esters of oligosaccharides such as sucrose, lactose and the like; oleic acid or linoleic acid esters of sugar derivatives such as sorbitol, mannitol, dulcitol, xylitol, erythritol etc. and the like. In the compound, all the hydroxyl groups in an alcohol having a sugar backbone may be esterified, or some of the hydroxyl groups in an alcohol having a sugar backbone may be partially esterified. These esters can be obtained by adjusting the preparation molar ratio of fatty acid relative to an alcohol having a sugar backbone.

Here, when j and k are each 0, X has a carbon number of not more than 3 and l+m+n=2, namely, an ester of ethyleneglycol or propyleneglycol and oleic acid or linoleic acid is not preferable, since it influences the trunk, branches and leaves of trees, even though the efficacy on the male organ is sharp.

The oleic acid derivative or linoleic acid derivative of the present invention can be diluted when in use by adding water. When the oleic acid derivative and linoleic acid derivative of the present invention have an HLB of 12 or below, they are mostly hardly water-soluble, and the diluted product by adding water becomes an emulsion. When producing an emulsion, the oleic acid derivative or linoleic acid derivative itself functions as a surfactant, which is effective for formation of emulsion. An emulsion may also be produced by adding a generally-used surfactant.

The concentration of an oleic acid derivative or linoleic acid derivative to be contained in the emulsion is preferably 0.5-30 wt %, more preferably 1-20 wt %. When it is not less than 20 wt %, the emulsion needs to be used immediately after preparation, since it has low stability. When it is not less than 30 wt %, a stable emulsion cannot be obtained.

When the oleic acid derivative and linoleic acid derivative of the present invention have an HLB greater than 12, they are mostly water-soluble, the diluted product by adding water becomes an aqueous solution. The concentration of an oleic acid derivative or linoleic acid derivative to be contained in the aqueous solution is preferably not less than 0.5 wt %, more preferably not less than 1 wt %. When it is less than 0.5 wt %, the amount thereof to be sprayed increases to achieve the effect.

The surfactant to be added to an emulsion may be any as long as it is generally used as an emulsifier, and a non-ionic surfactant is particularly preferable. Examples of the non-ionic surfactant include polyoxyethylene alkyl ether type non-ionic surfactant, polyoxyethylene fatty acid ester type non-ionic surfactant, polyoxyethylene fatty acid sorbitan ester type non-ionic surfactant, polyoxyethylene hydrogenated castor oil type non-ionic surfactant, polyoxyethyleneglycerol fatty acid ester type non-ionic surfactant, polyglycerol fatty acid ester type non-ionic surfactant and the like.

The agent for suppressing pollen dispersal which has been formulated as an emulsion or an aqueous solution in such manner can be, for example, sprayed from a helicopter etc. to suppress dispersal of pollen in a wide area.

The agent for suppressing pollen dispersal of the present invention may be sprayed on, for example, *Cryptomeria japonica* in any period after differentiation of the male flower bud, and can be sprayed over a comparatively long period of from August when male flower buds are in the initial period of bud differentiation process to October-November when the pollen grains are in the formation period, whereby the dispersal of pollen in the next spring can be effectively suppressed.

EXAMPLES

The present invention is explained in more detail in the following by referring to Examples, which are not to be construed as limitative.

Evaluation 1 (Immersion Test of *Cryptomeria japonica*)

First, as agents to be used for an immersion test of *Cryptomeria japonica*, fatty acid derivative, fatty acid, polyoxyalkylene derivative, fats and oils and the like shown in Tables 1 and 2 were prepared. Next, many branches (length about 10 cm) of *Cryptomeria japonica* with 15 male flower buds on the tip were taken from the same tree of *Cryptomeria japonica*, and each group (five leaves for one group) was immersed in the agents (100 ml) of Tables 1 and 2. After immersing for about 1 min, the branches were taken out from the liquid and placed in a beaker. Browning changes were inspected visually on the male flower buds and needle leaves after one week. The test was performed using *Cryptomeria japonica* of August and November. The results of August are shown in Table 3 and the results of November are shown in Table 4.

Sodium oleate, partial ester of stearic acid and glycerol, ester of stearic acid or palmitic acid and polyvalent alcohol, and ester of stearic acid and sorbitol used in Comparative Examples here are solids at room temperature. Thus, sodium oleate was used as an aqueous solution obtained by dissolving in water to an active ingredient concentration of 5%, and the partial ester of stearic acid and glycerol, the ester of stearic acid or palmitic acid and polyvalent alcohol, and the ester of stearic acid and sorbitol were used as a liquid oil obtained by dissolving in squalane that does not influence male flower buds, branches and leaves to an active ingredient concentration of 5%.

TABLE 1

| | | agent used for immersion test | fatty acid/polyoxyalkylene/ polyvalent alcohol (preparation molar ratio) |
|---|---|---|---|
| Ex. | 1 | polyoxyethylene oleic acid ester | 1/14/0 |
| | 2 | polyoxyethylene linoleic acid ester | 1/6/0 |
| | 3 | methoxypolyoxyethylene oleic acid ester | 1/14/0 |
| | 4 | polyoxyethylene dilinoleic acid ester | 2/14/0 |
| | 5 | polyoxyethylene-block-polyoxypropylene oleic acid ester (5% emulsion) | 1/17/0 (14 mol:oxyethylene, 3 mol:oxypropylene) |
| | 6 | polyoxyethylene sorbitan oleic acid ester | 1/20/1 |
| | 7 | polyoxyethylene sorbitol linoleic acid ester | 1/20/1 |
| | 8 | polyoxyethylene methylglucoside oleic acid ester | 1/20/1 |
| | 9 | polyoxyethylene glycerol linoleic acid ester | 1/20/1 |
| Comp. Ex. | 1 | oleic acid | — |
| | 2 | sodium oleate (5% aqueous solution) | — |
| | 3 | linoleic acid | — |
| | 4 | polyoxyethylene stearic acid ester | 1/14/0 |
| | 5 | polyoxyethylene linolenic acid ester | 1/6/0 |
| | 6 | polyoxyethylene sorbitol | 0/20/1 |
| | 7 | polyoxyethylene sorbitan palmitic acid ester | 1/20/1 |
| | 8 | olive oil | — |
| | 9 | sunflower oil | — |

TABLE 2

| | | fatty acid (or salt thereof) | polyvalent alcohol | fatty acid/polyvalent alcohol (preparation molar ratio) |
|---|---|---|---|---|
| Ex. | 10 | oleic acid | glycerol | 1/1 |
| | 11 | linoleic acid | glycerol | 2/1 |
| | 12 | oleic acid | glycerol | 2/1 |
| | 13 | linoleic acid | glycerol | 1/1 |
| | 14 | linoleic acid | 1,3-butanediol | 1/1 |
| | 15 | oleic acid | pentaerythritol | 3/1 |
| | 16 | oleic acid | neopentylglycol | 1/1 |
| | 17 | linoleic acid | trimethylolpropane | 2/1 |
| | 18 | oleic acid | hexyleneglycol | 1/1 |
| | 19 | linoleic acid | dipropyleneglycol | 1/1 |
| | 20 | linoleic acid | 2,2'-diethyl-2,2'-(oxydimethyl)bis-(propane-1,3-diol) | 2/1 |
| | 21 | oleic acid | diglycerol | 2/1 |
| | 22 | oleic acid | sorbitol | 3/1 |
| | 23 | linoleic acid | glucose | 2/1 |
| | 24 | oleic acid | fructose | 3/1 |
| | 25 | linoleic acid | erythritol | 2/1 |
| | 26 | oleic acid | sucrose | 3/1 |
| | 27 | oleic acid | sorbitol | 2/1 |
| | 28 | oleic acid | sorbitol | 6/1 |
| | 29 | linoleic acid | lactose | 4/1 |
| | 30 | oleic acid | xylitol | 5/1 |
| | 31 | oleic acid | mannitol | 2/1 |
| Comp. Ex. | 10 | stearic acid (5% squalane solution) | diglycerol | 1/1 |
| | 11 | linolenic acid | diglycerol | 1/1 |
| | 12 | oleic acid | diglycerol | 3/1 |
| | 13 | linoleic acid | diglycerol | 3/1 |
| | 14 | stearic acid (5% squalane solution) | pentaerythritol | 3/1 |
| | 15 | palmitic acid (5% squalane solution) | neopentylglycol | 1/1 |
| | 16 | linolenic acid | trimethylolpropane | 2/1 |
| | 17 | linolenic acid | didiglycerol | 2/1 |
| | 18 | stearic acid (5% squalane solution) | sorbitol | 2/1 |
| | 19 | linolenic acid | sorbitol | 2/1 |

TABLE 3

| change of state of male flower bud and needle leaf (August) | | | |
|---|---|---|---|
| | | male flower bud | needle leaf |
| Example | 1 | browned | no change |
| | 2 | markedly browned | no change |
| | 3 | browned | no change |
| | 4 | markedly browned | no change |
| | 5 | browned | no change |
| | 6 | browned | no change |
| | 7 | browned | ho change |
| | 8 | browned | no change |
| | 9 | browned | no change |
| | 10 | markedly browned | no change |
| | 11 | markedly browned | no change |
| | 12 | markedly browned | no change |
| | 13 | markedly browned | no change |
| | 14 | browned | no change |
| | 15 | markedly browned | no change |
| | 16 | browned | no change |
| | 17 | markedly browned | no change |
| | 18 | browned | no change |
| | 19 | browned | no change |
| | 20 | markedly browned | no change |
| | 21 | markedly browned | no change |
| | 22 | markedly browned | no change |
| | 23 | markedly browned | no change |
| | 24 | markedly browned | no change |

TABLE 3-continued

| change of state of male flower bud and needle leaf (August) | | | |
|---|---|---|---|
| | | male flower bud | needle leaf |
| | 25 | markedly browned | no change |
| | 26 | browned | no change |
| | 27 | markedly browned | no change |
| | 28 | browned | no change |
| | 29 | browned | no change |
| | 30 | browned | no change |
| | 31 | markedly browned | no change |
| Comparative Example | 1 | markedly browned | no change |
| | 2 | markedly browned | no change |
| | 3 | markedly browned | no change |
| | 4 | no change | browned |
| | 5 | markedly browned | browned |
| | 6 | no change | no change |
| | 7 | no change | browned |
| | 8 | browned | no change |
| | 9 | markedly browned | no change |
| | 10 | no change | browned |
| | 11 | markedly browned | browned |
| | 12 | browned | no change |
| | 13 | browned | no change |
| | 14 | no change | browned |
| | 15 | no change | browned |
| | 16 | markedly browned | browned |
| | 17 | markedly browned | browned |
| | 18 | browned | browned |
| | 19 | markedly browned | browned |

TABLE 4

| change of state of male flower bud and needle leaf (November) | | | |
|---|---|---|---|
| | | male flower bud | needle leaf |
| Example | 1 | browned | no change |
| | 2 | markedly browned | no change |
| | 3 | browned | no change |
| | 4 | markedly browned | no change |
| | 5 | browned | no change |
| | 6 | browned | no change |
| | 7 | browned | no change |
| | 8 | browned | no change |
| | 9 | browned | no change |
| | 10 | markedly browned | no change |
| | 11 | markedly browned | no change |
| | 12 | markedly browned | no change |
| | 13 | markedly browned | no change |
| | 14 | browned | no change |
| | 15 | markedly browned | no change |
| | 16 | browned | no change |
| | 17 | markedly browned | no change |
| | 18 | browned | no change |
| | 19 | browned | no change |
| | 20 | markedly browned | no change |
| | 21 | markedly browned | no change |
| | 22 | markedly browned | no change |
| | 23 | markedly browned | no change |
| | 24 | markedly browned | no change |
| | 25 | markedly browned | no change |
| | 26 | browned | no change |
| | 27 | markedly browned | no change |
| | 28 | browned | no change |
| | 29 | browned | no change |
| | 30 | browned | no change |
| | 31 | markedly browned | no change |
| Comparative Example | 1 | no change | no change |
| | 2 | no change | no change |
| | 3 | no change | no change |
| | 4 | no change | browned |
| | 5 | markedly browned | browned |
| | 6 | no change | no change |
| | 7 | no change | browned |
| | 8 | no change | no change |
| | 9 | no change | no change |

TABLE 4-continued

| change of state of male flower bud and needle leaf (November) | | |
|---|---|---|
| | male flower bud | needle leaf |
| 10 | no change | browned |
| 11 | markedly browned | browned |
| 12 | no change | no change |
| 13 | no change | no change |
| 14 | no change | browned |
| 15 | no change | browned |
| 16 | markedly browned | browned |
| 17 | markedly browned | browned |
| 18 | no change | browned |
| 19 | markedly browned | browned |

From the results shown in Tables 3 and 4, it was confirmed in the Examples of the present invention that in both August and November, the efficacy on the male flower bud was sharp and needle leaves were not influenced. On the contrary, in Comparative Examples 1, 2 and 3, since oleic acid, sodium oleate and linoleic acid were used as agents, respectively, no effect was obtained for the male flower bud of November.

In Comparative Examples 4 and 7, since stearic acid and palmitic acid derivative was used, no effect was obtained for the male flower buds of both August and November, and the needle leaf was adversely influenced. In Comparative Example 5, since linolenic acid derivative was used as an agent, an effect was obtained for the male flower buds of both August and November, but the needle leaf was adversely influenced. In Comparative Example 6, since fatty acid was not used, the male flower bud and the needle leaf of both August and November were not influenced. In Comparative Examples 8 and 9, since olive oil and sunflower oil were used as agents, respectively, no effect could be obtained for the male flower bud of November.

In Comparative Example 10, since the partial ester of stearic acid and glycerol was used as an agent, no effect was obtained for the male flower bud of both August and November, and the needle leaf was adversely influenced. In Comparative Example 11, since the partial ester of linolenic acid and glycerol was used as an agent, an effect was obtained for the male flower bud in both August and November, but the needle leaf was adversely influenced. In Comparative Example 12, while the ester of oleic acid and glycerol was used as an agent, since 3 hydroxyl groups of glycerol were all esterified with oleic acid, no effect was obtained for the male flower bud of November. In Comparative Example 13, while the ester of linoleic acid and glycerol was used as an agent, since three hydroxyl groups of glycerol were all esterified with linoleic acid, no effect was obtained for the male flower bud of November.

In Comparative Examples 14 and 15, since the ester of stearic acid and palmitic acid and a polyvalent alcohol having a carbon number of 4 or more was used as an agent, no effect was obtained for the male flower bud of both August and November, and the needle leaf was adversely influenced. In Comparative Examples 16 and 17, since the ester of linolenic acid and a polyvalent alcohol having a carbon number of 4 or more was used as an agent, an effect was obtained for the male flower bud of both August and November, but the needle leaf was adversely influenced.

In Comparative Example 18, since the ester of stearic acid and sorbitol was used as an agent, no effect was obtained for the male flower bud of November, and the needle leaf was adversely influenced. In Comparative Example 19, since the ester of linolenic acid and sorbitol was used as an agent, the effect could be obtained for the male flower bud of both August and November, but the needle leaf was adversely influenced.

Evaluation 2 (Evaluation of Dilution Type Agent for Suppressing Pollen Dispersal)

A diluted solution or an emulsion having the formulation shown in Table 5 was prepared, and the effect of each solution for *Cryptomeria japonica* was evaluated in the same manner as in Evaluation 1. That is, many branches (length about 10 cm) of *Cryptomeria japonica* with 15 male flower buds on the tip were taken from the same tree of *Cryptomeria japonica*, and five branches for one group were immersed in the agents (100 ml) of Table 5. After immersing for about 1 min, the branches were taken out from the liquid and placed in a beaker such that the section was immersed in water. Browning changes were inspected visually on the male flower buds and needle leaves after one week. The test was performed using *Cryptomeria japonica* of August and November. The results are shown in Table 6. The solution was prepared as follows.

(Preparation Method of Solution)

The agents in the amounts shown in Table 5 (glycerol was added as stabilizer for emulsification) and water were stirred at 70° C., mixed, treated by a homogenizer (manufactured by MIZUHO Industrial CO., Ltd., QUICK HOMO MIXER LR-1) at 7000 rpm for 3 min, and cooled with stirring.

(Evaluation of Stability of Solution)

Each solution was placed in a thermostatic tank which repeated −5° C. and 40° C. alternately for 12 hr each for 1 month, and the solution state was observed and evaluated as follows.

○: good stability (no change in appearance of solution for 1 month)

x: bad stability (solution separates within 1 month)

(Evaluation of Stability of the Solution at High Temperature)

Each solution was placed in a thermostatic tank which repeated −5° C. and 80° C. alternately for 12 hr each for 1 month, and the solution state was observed and evaluated as follows.

○: good stability (no change in appearance of solution for 1 month)

x: bad stability (solution separates within 1 month)

TABLE 5

| | | agent of Ex. 2 (HLB = 10.2) | agent of Ex. 6 (HLB = 15.0) | agent of Ex. 12 | agent of Ex. 15 | agent of Ex. 21 | agent of Ex. 22 | surfactant (note 1) | glycerol | water | solution state |
|---|---|---|---|---|---|---|---|---|---|---|---|
| Blending Example | 1 | 10 | 5 | 0 | 0 | 0 | 0 | 0 | 3 | 82 | emulsion |
| | 2 | 5 | 0 | 0 | 0 | 0 | 0 | 0 | 0 | 95 | emulsion |
| | 3 | 0 | 40 | 0 | 0 | 0 | 0 | 0 | 0 | 60 | transparent uniform solution |
| | 4 | 0 | 5 | 0 | 0 | 0 | 0 | 0 | 0 | 95 | transparent uniform solution |
| | 5 | 0 | 0 | 1 | 0 | 0 | 0 | 5 | 3 | 91 | not observed |
| | 6 | 0 | 5 | 5 | 0 | 0 | 0 | 0 | 3 | 87 | not observed |

TABLE 5-continued

| | agent of Ex. 2 (HLB = 10.2) | agent of Ex. 6 (HLB = 15.0) | agent of Ex. 12 | agent of Ex. 15 | agent of Ex. 21 | agent of Ex. 22 | surfactant (note 1) | glycerol | water | solution state |
|---|---|---|---|---|---|---|---|---|---|---|
| 7 | 0 | 5 | 10 | 0 | 0 | 0 | 0 | 3 | 82 | not observed |
| 8 | 0 | 0 | 20 | 0 | 0 | 0 | 5 | 3 | 72 | not observed |
| 9 | 0 | 0 | 0 | 1 | 0 | 0 | 5 | 3 | 91 | not observed |
| 10 | 0 | 0 | 0 | 0 | 5 | 0 | 5 | 3 | 87 | not observed |
| 11 | 0 | 0 | 0 | 10 | 0 | 0 | 5 | 3 | 82 | not observed |
| 12 | 0 | 0 | 0 | 0 | 20 | 0 | 5 | 3 | 72 | not observed |
| 13 | 0 | 0 | 0 | 0 | 0 | 1 | 5 | 3 | 91 | not observed |
| 14 | 0 | 5 | 0 | 0 | 0 | 5 | 0 | 3 | 87 | not observed |
| 15 | 0 | 5 | 0 | 0 | 0 | 10 | 0 | 3 | 82 | not observed |
| 16 | 0 | 0 | 0 | 0 | 0 | 20 | 5 | 3 | 72 | not observed |
| 17 | 0.2 | 0.1 | 0 | 0 | 0 | 0 | 0 | 3 | 96.7 | emulsion |
| 18 | 35 | 0 | 0 | 0 | 0 | 0 | 0 | 3 | 62 | emulsion |
| 19 | 0 | 0.3 | 0 | 0 | 0 | 0 | 0 | 0 | 99.7 | transparent uniform solution |
| 20 | 0 | 0 | 0.3 | 0 | 0 | 0 | 5 | 3 | 91.7 | not observed |
| 21 | 0 | 0 | 35 | 0 | 0 | 0 | 5 | 3 | 57 | not observed |
| 22 | 0 | 0 | 0 | 0.3 | 0 | 0 | 5 | 3 | 91.7 | not observed |
| 23 | 0 | 0 | 0 | 0 | 35 | 0 | 5 | 3 | 57 | not observed |
| 24 | 0 | 0 | 0 | 0 | 0 | 0.3 | 5 | 3 | 91.7 | not observed |
| 25 | 0 | 0 | 0 | 0 | 0 | 35 | 5 | 3 | 57 | not observed |

note 1)
polyoxyethylene (40 mol) hydrogenated castor oil type non-ionic surfactant

TABLE 6

| | August | | November | | | |
|---|---|---|---|---|---|---|
| | male flower bud | needle leaf | male flower bud | needle leaf | stability | stability at high temperature |
| Blending Ex. 1 | markedly browned | no change | markedly browned | no change | ○ | x |
| Blending Ex. 2 | markedly browned | no change | markedly browned | no change | ○ | x |
| Blending Ex. 3 | markedly browned | no change | markedly browned | no change | ○ | ○ |
| Blending Ex. 4 | markedly browned | no change | markedly browned | no change | ○ | ○ |
| Blending Ex. 5 | markedly browned | no change | markedly browned | no change | ○ | not performed |
| Blending Ex. 6 | markedly browned | no change | markedly browned | no change | ○ | not performed |
| Blending Ex. 7 | markedly browned | no change | markedly browned | no change | ○ | not performed |
| Blending Ex. 8 | markedly browned | no change | markedly browned | no change | ○ | not performed |
| Blending Ex. 9 | markedly browned | no change | markedly browned | no change | ○ | not performed |
| Blending Ex. 10 | markedly browned | no change | markedly browned | no change | ○ | not performed |
| Blending Ex. 11 | markedly browned | no change | markedly browned | no change | ○ | not performed |
| Blending Ex. 12 | markedly browned | no change | markedly browned | no change | ○ | not performed |
| Blending Ex. 13 | markedly browned | no change | markedly browned | no change | ○ | not performed |
| Blending Ex. 14 | markedly browned | no change | markedly browned | no change | ○ | not performed |
| Blending Ex. 15 | markedly browned | no change | markedly browned | no change | ○ | not performed |
| Blending Ex. 16 | markedly browned | no change | markedly browned | no change | ○ | not performed |
| Blending Ex. 17 | browned | no change | browned | no change | ○ | x |
| Blending Ex. 18 | markedly browned | no change | markedly browned | no change | x | x |
| Blending Ex. 19 | browned | no change | browned | no change | ○ | ○ |
| Blending Ex. 20 | browned | no change | browned | no change | ○ | not performed |
| Blending Ex. 21 | markedly browned | no change | markedly browned | no change | x | not performed |

TABLE 6-continued

| | August | | November | | | |
|---|---|---|---|---|---|---|
| | male flower bud | needle leaf | male flower bud | needle leaf | stability | stability at high temperature |
| Blending Ex. 22 | browned | no change | browned | no change | ○ | not performed |
| Blending Ex. 23 | markedly browned | no change | markedly browned | no change | x | not performed |
| Blending Ex. 24 | browned | no change | browned | no change | ○ | not performed |
| Blending Ex. 25 | markedly browned | no change | markedly browned | no change | x | not performed |

From the results shown in Table 6, it was confirmed that in both August and November, the efficacy on the male flower bud was sharp and needle leaves were not influenced, in addition a stable diluted solution was obtained. In contrast, in Blending Examples 18, 21, 23 and 25, since the amount of the agent of the Examples to be blended exceeded 30 wt %, the stability of the emulsion was poor.

This application is based on patent application Nos. 2008-28253 (filing date: Feb. 8, 2008), 2008-28254 (filing date: Feb. 8, 2008), 2008-36632 (filing date: Feb. 18, 2008) and 2008-36633 (filing date: Feb. 18, 2008) filed in Japan, the contents of which are incorporated in full herein.

The invention claimed is:

1. A method for suppressing pollen dispersal, comprising spraying or applying to a male organ of a tree an effective amount of an oleic acid derivative or linoleic acid derivative represented by the following formula (I)

(I)

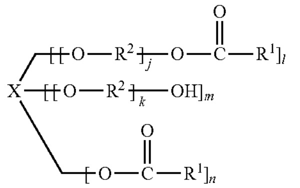

wherein $R^1$ are residues of an oleic acid ester or a linoleic acid ester, which may be of the same kind or different kinds, O—$R^2$ are oxyalkylene groups having a carbon number of 2 to 4, which may be of one kind of two or more kinds, and when they are of two or more kinds, they may be block adducts or random adducts;

j and k are 0,

X is a polyvalent organic group having a carbon number of 4 or more, 1 is 0, n is 2 or 3, and m+n is 3, 4, 5, or 6, thereby suppressing pollen dispersal.

2. The method for suppressing pollen dispersal according to claim 1, wherein the oleic acid derivative or linoleic acid derivative is comprised of a ester of oleic acid or linoleic acid and glycerol.

3. The method for suppressing pollen dispersal according to claim 2, wherein the oleic acid derivative or linoleic acid derivative is in an emulsion comprising a ester of oleic acid or linoleic acid and glycerol in a proportion of 0.5-30 wt %.

4. The method for suppressing pollen dispersal according to claim 1, wherein the oleic acid derivative or linoleic acid derivative is comprised of an ester of oleic acid or linoleic acid and a polyvalent alcohol having a carbon number of not less than 4.

5. The method for suppressing pollen dispersal according to claim 4, wherein the oleic acid derivative or linoleic acid derivative is in an emulsion comprising an ester of oleic acid or linoleic acid and a polyvalent alcohol having a carbon number of not less than 4 in a proportion of 0.5-30 wt %.

6. The method for suppressing pollen dispersal according to claim 1, wherein the oleic acid derivative or linoleic acid derivative is comprised of an ester of oleic acid or linoleic acid and an alcohol having a sugar backbone.

7. The method for suppressing pollen dispersal according to claim 6, wherein the oleic acid derivative or linoleic acid derivative is in an emulsion comprising an ester of oleic acid or linoleic acid and an alcohol having a sugar backbone in a proportion of 0.5-30 wt %.

* * * * *